United States Patent
Altmann et al.

(10) Patent No.: US 7,831,076 B2
(45) Date of Patent: Nov. 9, 2010

(54) COLORING ELECTROANATOMICAL MAPS TO INDICATE ULTRASOUND DATA ACQUISITION

(75) Inventors: Andres Claudio Altmann, Haifa (IL); Assaf Govari, Haifa (IL); Dina Kirshenbaum, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 880 days.

(21) Appl. No.: 11/608,506

(22) Filed: Dec. 8, 2006

(65) Prior Publication Data

US 2008/0137927 A1 Jun. 12, 2008

(51) Int. Cl.
G06K 9/00 (2006.01)
A61B 5/05 (2006.01)

(52) U.S. Cl. .................. 382/128; 382/154; 600/424

(58) Field of Classification Search .......... 382/100, 382/128, 129, 130, 131, 132, 133, 134, 154, 382/162, 165, 168, 180, 181, 184, 199, 203, 382/224, 232, 254, 274, 276, 285–291, 305, 382/312; 600/459, 463, 424, 34; 378/21
See application file for complete search history.

(56) References Cited

U.S. PATENT DOCUMENTS

| | | | |
|---|---|---|---|
| 6,066,096 A | 5/2000 | Smith et al. | |
| 6,332,089 B1 * | 12/2001 | Acker et al. | 600/424 |
| 6,556,695 B1 * | 4/2003 | Packer et al. | 382/128 |
| 6,618,612 B1 | 9/2003 | Acker et al. | |
| 6,645,145 B1 | 11/2003 | Dreschel et al. | |
| 6,650,927 B1 | 11/2003 | Keidar | |
| 6,690,963 B2 | 2/2004 | Ben-Haim et al. | |
| 6,716,166 B2 | 4/2004 | Govari | |
| 6,773,402 B2 * | 8/2004 | Govari et al. | 600/459 |
| 6,788,967 B2 | 9/2004 | Ben-Haim et al. | |
| 6,892,091 B1 | 5/2005 | Ben-Haim et al. | |
| 7,517,318 B2 * | 4/2009 | Altmann et al. | 600/459 |
| 7,604,601 B2 * | 10/2009 | Altmann et al. | 600/463 |
| 2003/0231789 A1 | 12/2003 | Willis et al. | |
| 2004/0068178 A1 * | 4/2004 | Govari | 600/424 |
| 2004/0147920 A1 * | 7/2004 | Keidar | 606/34 |

(Continued)

FOREIGN PATENT DOCUMENTS

EP 1720038 11/2006

(Continued)

OTHER PUBLICATIONS

Partial European Search Report re: EP07254746 dated Aug. 7, 2008.

(Continued)

*Primary Examiner*—Seyed Azarian
(74) *Attorney, Agent, or Firm*—Louis J. Capezzuto (57) ABSTRACT

During acquisition of ultrasound data in a medical imaging procedure, three-dimensional model of a structure being imaged, e.g., an electroanatomical map, is co-displayed and visually marked, to indicate progress of data acquisition. The plane of intersection successive two-dimensional images are marked on the as a line or colored region on the three-dimensional model. This display enables the operator to determine regions where sufficient data have been captured, and guides the operator to areas where additional data collection is still needed. Various color schemes are used to indicate the relative sufficiency of data collection.

23 Claims, 6 Drawing Sheets

U.S. PATENT DOCUMENTS

2006/0239527 A1   10/2006   Krishnan et al.

FOREIGN PATENT DOCUMENTS

WO   WO 99/60921   12/1999

OTHER PUBLICATIONS

Pending U.S. Appl. No. 11/115,002, Biosense Webster, Inc.
Pending U.S. Appl. No. 11/215,435, Biosense Webster, Inc.
Pending U.S. Appl. No. 11/262,217, Biosense Webster, Inc.
Sermesant, M., et al. Simulation of Cardiac Pathologies Using An Electromechanical Biventricular Model and XMR Interventionaol Imaging, Medical Image Analysis vol. 9, No. 5 (2005) pp. 467-480.
Yabe, T. Quantitative Measurements of Cardiac Phosphorus Metabolites in Coronary Artery Disease by $^{31}$P Magnetic Resonance Spectrosocpy, Circulation, 1995;92:15-23.

* cited by examiner

FIG. 7

COLORING ELECTROANATOMICAL MAPS TO INDICATE ULTRASOUND DATA ACQUISITION

BACKGROUND OF THE INVENTION

1. Field of the Invention

This invention relates generally to mapping and reconstruction of body organs. More particularly, this invention relates to imaging internal body organs, such as the heart.

2. Description of the Related Art

Ultrasound imaging is now well established as a modality for imaging the heart. For example, U.S. Pat. No. 6,066,096, whose disclosure is incorporated herein by reference, describes an imaging probe for volumetric intraluminal ultrasound imaging. The probe, configured to be placed inside a patient's body, includes an elongated body having proximal and distal ends. An ultrasonic transducer phased array is connected to and positioned on the distal end of the elongated body. The ultrasonic transducer phased array is positioned to emit and receive ultrasonic energy for volumetric forward scanning from the distal end of the elongated body. The ultrasonic transducer phased array includes a plurality of sites occupied by ultrasonic transducer elements.

However, many physicians find it difficult to interpret ultrasound images, which typically appear as a two-dimensional fan-shaped pattern. Although the physician knows what anatomical features should appear in a display produced by an ultrasound catheter, he may not be able to match these features with the bright and dark areas of the fan.

It has been proposed to improve medical image interpretation by superimposing images acquired by different modalities in registration. For example, U.S. Pat. No. 6,556,695, issued to Packer et al., suggests that a magnetic resonance image can be acquired, and then registered with a subsequently acquired electrical activation map or ultrasound image.

SUMMARY OF THE INVENTION

In order to assist the physician in performing a realtime cardiac imaging procedure, a three-dimensional image of the heart may be rendered during acquisition. However, this blocks the user's view of the heart chamber by other tissue reflection, e.g., from other chambers or organs. Therefore, it is difficult for the user to determine when adequate image data have been acquired or whether details are still missing.

According to disclosed embodiments of the invention, a three-dimensional representation of the structure, such as a functional map, e.g., an electroanatomical map, is displayed and marked, typically by application of pseudocolor, during acquisition of ultrasound data in order to show the progress of data acquisition. For example, the planes of intersection of successive ultrasound two-dimensional fans that are acquired may be marked on an electroanatomical map as lines or colored regions on the map surface. This display enables the operator to determine regions where sufficient ultrasound data have been captured, and guides the operator to areas of the heart chamber where additional data collection is still needed. Various color schemes are used to indicate the relative sufficiency of data collection.

An embodiment of the invention provides a computer-assisted method for producing images of a living subject, which is carried out by displaying a three-dimensional model of a surface of a structure in a body of the subject, acquiring a sequence of two-dimensional anatomic images of at least a portion of the structure, and while acquiring the sequence, marking the three-dimensional model to show respective intersections of the image planes with the surface.

In an aspect of the method, the three-dimensional model may be a computed tomographic image or a magnetic resonance image, which is automatically registered with the image planes.

Another aspect of the method includes displaying the three-dimensional model and the respective intersections of the image planes with the surface on the three-dimensional model.

According to an additional aspect of the method, a pseudocolor is displayed on the respective intersections of the image planes with the surface.

Yet another aspect of the method includes interpolating areas of the three-dimensional model between the respective intersections, marking the interpolated areas, and displaying the interpolated areas.

Another aspect of the method includes reconstructing a three-dimensional anatomic image of the structure from the two-dimensional anatomic images, and displaying at least a portion of the three-dimensional anatomic image with the three-dimensional model.

According to still another aspect of the method, the displayed portion of the three-dimensional anatomic image does not extend beyond a predefined distance from a surface of the three-dimensional model.

According to one aspect of the method, the structure is a heart and the three-dimensional model is an anatomical map.

In other aspects of the method, the two-dimensional anatomic images can be acquired by real-time three-dimensional ultrasound imaging, realtime computed tomographic imaging, or realtime magnetic resonance imaging.

Other embodiments of the invention provide apparatus for carrying out the above-described method.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

System Overview

Figure 1:
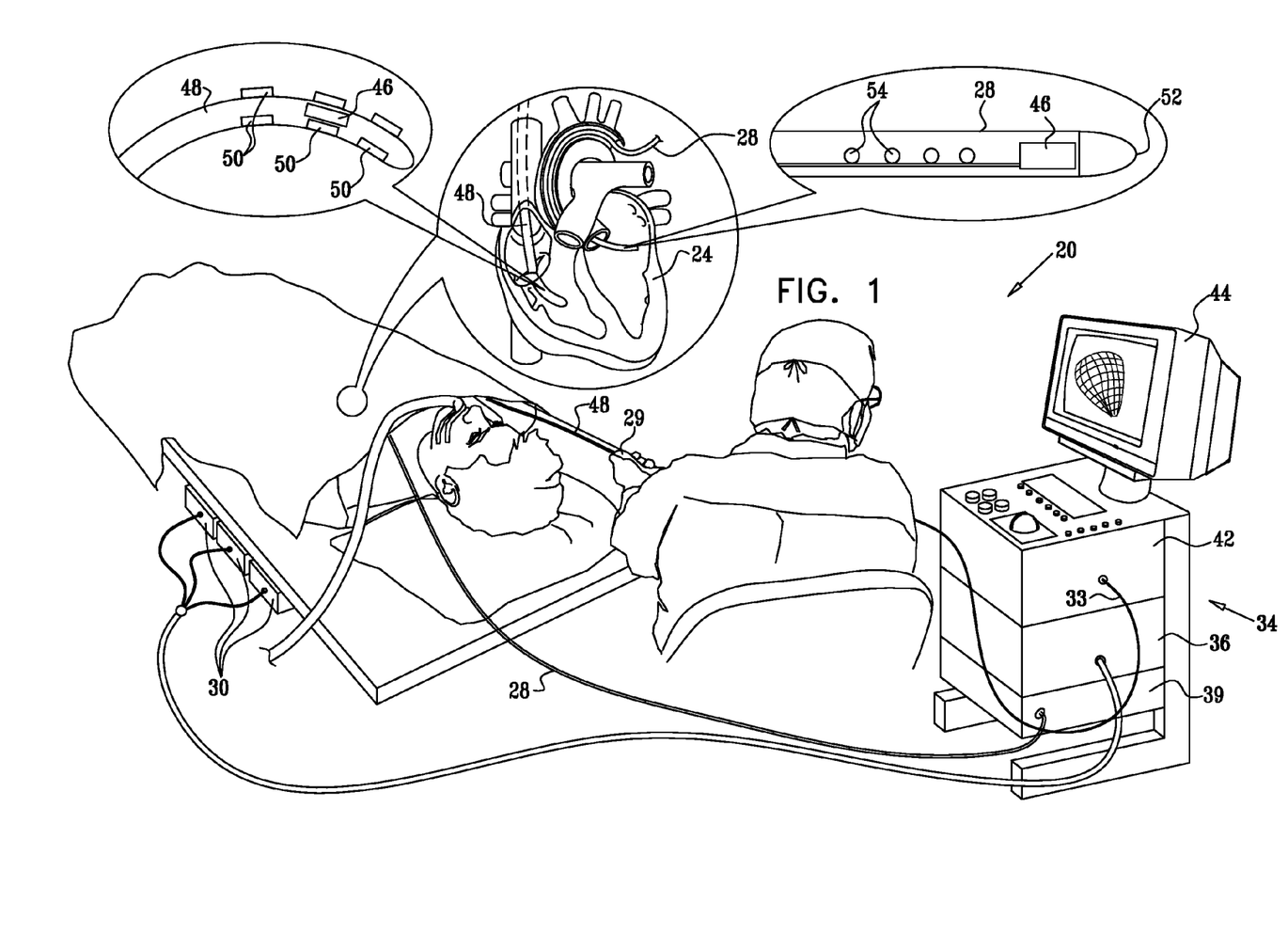
FIG. 1 illustrates a system for imaging and mapping a heart of a patient in accordance with a disclosed embodiment of the invention.

Turning now to the drawings, reference is initially made to FIG. 1, which is an illustration of a system 20 for imaging and generating electrical activation maps of a heart 24 of a patient, and which is suitable for performing diagnostic or therapeutic procedures involving the heart 24, in accordance with an embodiment of the present invention.

While the principles of the invention are disclosed with reference to cardiac imaging, the techniques described may be adapted for use for imaging other organs using a manually or automatically controlled probe, particularly hollow organs, such as the bladder, which may be imaged using an ultrasound catheter.

The system 20 comprises a catheter 28, which is percutaneously inserted by a physician into a chamber or vascular structure of the heart. The catheter 28 typically comprises a handle 29 for operation of the catheter by the physician. Suitable controls on the handle 29 enable the physician to steer, position and orient the distal end of the catheter as desired.

The system 20 enables the physician to perform a variety of mapping and imaging procedures. These procedures comprise, for example, the following techniques, which are described in further detail in copending, commonly assigned application Ser. Nos. 11/115,002 and 11/262,217, the disclosures of which are herein incorporated by reference:

display real-time or near real-time two-dimensional images, e.g. ultrasound images;

reconstruct three-dimensional models of a target structure in the patient's body, based on two-dimensional ultrasound images;

register, overlay and display a parametric map, such as an electrophysiological information map or an electroanatomical map on the reconstructed three-dimensional model;

register, overlay and display a three-dimensional image acquired from an external system on the reconstructed three-dimensional model; and register and display two-dimensional ultrasound images on a three-dimensional image acquired from an external system.

The system 20 comprises a positioning subsystem that measures three-dimensional location information and orientation coordinates of the catheter 28 with up to six degrees of freedom. The positioning subsystem may comprise a magnetic position tracking system that determines the position and orientation of the catheter 28. The positioning subsystem generates magnetic fields in a predefined working volume its vicinity and senses these fields at the catheter. The positioning subsystem typically comprises a set of external radiators, such as field generating coils 30, which are located in fixed, known positions external to the patient. The coils 30 generate fields, typically electromagnetic fields, in the vicinity of the heart 24.

In an alternative embodiment, a radiator in the catheter, such as a coil, generates electromagnetic fields, which are received by sensors (not shown) outside the patient's body.

The position sensor transmits, in response to the sensed fields, position-related electrical signals over cables 33 running through the catheter to a console 34. Alternatively, the position sensor may transmit signals to the console 34 over a wireless link. The console 34 comprises a positioning processor 36 that calculates the location and orientation of the catheter 28 based on the signals sent by a location sensor 46. The positioning processor 36 typically receives, amplifies, filters, digitizes, and otherwise processes signals from the catheter 28. Images produced by the system 20 are displayed on a monitor 44.

Some position tracking systems that may be used for this purpose are described, for example, in U.S. Pat. Nos. 6,690,963, 6,618,612 and 6,332,089, and U.S. patent application Publications 2004/0147920, and 2004/0068178, whose disclosures are incorporated herein by reference. Although the positioning subsystem shown in FIG. 1 uses magnetic fields, the methods described below may be implemented using any other suitable positioning subsystem, such as systems based on acoustic or ultrasonic measurements.

For ultrasound image generation, the system 20 may employ the catheters disclosed in U.S. Pat. Nos. 6,716,166 and 6,773,402, whose disclosures are herein incorporated by reference, in order to acquire ultrasound images for display in near realtime ultrasound images concurrently with an image or representation of the position of a deployment catheter in the same or different sessions, and in many different combinations. Such catheters have acoustic transducers that are adapted for emitting sound waves, and receiving reflections from echogenic interfaces in the heart. The reflections are then analyzed to construct two-dimensional and three-dimensional images of the heart.

The system 20 comprises an ultrasound driver 39 that drives the ultrasound transducers of the catheter 28 when it functions as an ultrasound imaging catheter. One example of a suitable ultrasound driver that can be used for this purpose is an AN2300™ ultrasound system produced by Analogic Corporation, 8 Centennial Drive, Peabody, Mass. 01960. The ultrasound driver 39 may support different imaging modes such as B-mode, M-mode, CW Doppler and color flow Doppler, as are known in the art.

Optionally, the catheter 28 and another catheter 48 are both incorporated in the system 20 and inserted concurrently into the heart via different vascular approaches. In this example, the catheter 28 functions as a mapping catheter, and the catheter 48 functions as an ultrasound imaging catheter, using an array of acoustic transducers 50. Each has an instance of the location sensor 46 that is used to determine the position and orientation of the catheter within the body.

The system 20 contains electronic circuitry for generation of an electrical activation map, and can be used in conjunction with many specialized mapping catheters. A suitable mapping catheter for use as the catheter 28 is described in commonly assigned U.S. Pat. No. 6,892,091, whose disclosure is herein incorporated by reference. Briefly, the distal end of the mapping catheter includes a distally placed mapping electrode 52 for measuring the electrical properties of the heart tissue. The distal end of the mapping catheter further also includes an array of non-contact electrodes 54 for measuring far field electrical signals in the heart chamber.

Typically, the mapping catheter is introduced first, and an electrical activation map generated from its data. Afterward, an ultrasound imaging catheter is introduced. The two catheters may be introduced via the same or different vascular approaches.

In yet another alternative, a hybrid catheter, capable of both data acquisition suitable for electrical activation map generation, and also having ultrasound imaging functions can be used. Such catheters are described, for example, in U.S. Pat. Nos. 6,773,402, 6,788,967, and 6,645,145. Use of such catheters may permit the medical procedure to be shortened. In this alternative, only one catheter need be inserted. In all the alternatives, as explained in further detail below, the electrical activation map is usually acquired first, and then applied to the ultrasound images to assist in the interpretation of the latter. Suitable image registration techniques for coordinating the two modalities are disclosed in U.S. Pat. No. 6,650,927 and in co-pending application Ser. No. 11/215,435, both of common assignee herewith, and herein incorporated by reference.

Figure 2:
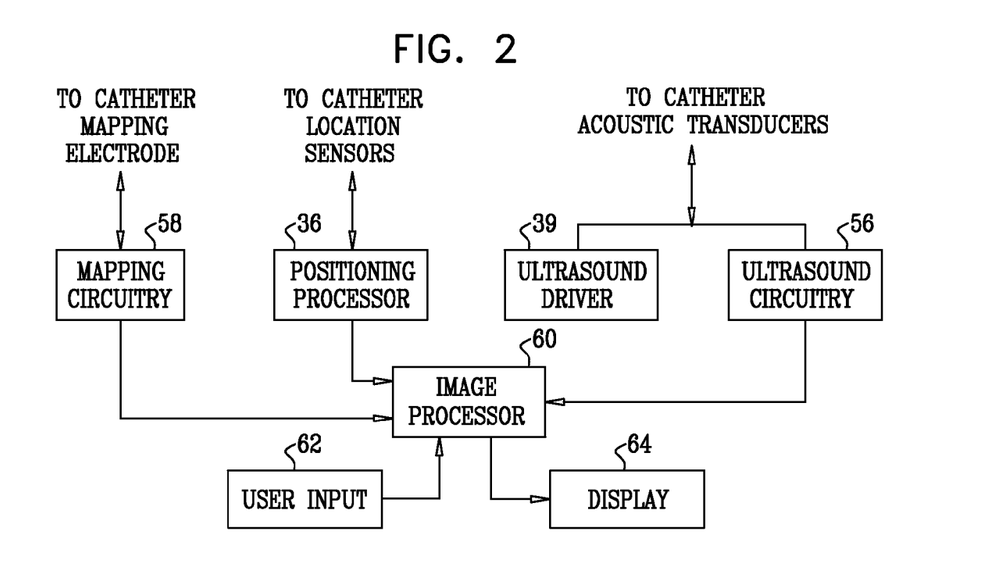
FIG. 2 is a block diagram illustrating further details of the system shown in FIG. 1 in accordance with a disclosed embodiment of the invention.

Reference is now made to FIG. 2, which is a block diagram illustrating further details of the system 20 (FIG. 1). As noted above, many elements of the system 20 can be realized as a general purpose or specialized computer that includes a processor and a memory that contains objects corresponding to the functional blocks depicted in FIG. 2. The positioning processor 36 is linked to location sensors that are placed near the distal tip of the cardiac catheter and performs location tracking.

The ultrasound driver 39, which drives the transducers 50 (FIG. 1) is cooperative with ultrasound circuitry 56, and produces two-dimensional ultrasound images.

An image processor 60 is linked to the mapping circuitry 58, the positioning processor 36, and the ultrasound circuitry 56. The image processor 60 can perform three-dimensional ultrasound image reconstruction, and is specialized for the automatic identification of cardiac topological features on the ultrasound images. In some embodiments, the image processor 60 may augment automatic identification of topologic features on the electrical activation map by the mapping circuitry 58, without operator assistance. The image processor 60 also performs image registration functions. Its operation is mediated via a user input 62. Its output is sent to a display 64.

A commercial unit suitable for use in the system 20, which is capable of generating an electrical activation map, is the CARTO XP EP Navigation and Ablation System, available from Biosense Webster, Inc., 3333 Diamond Canyon Road, Diamond Bar, Calif. 91765. Images acquired using different modalities can be registered for display using the CartoMerge™ image integration module, which is adapted for operation with the CARTO XP EP Navigation and Ablation System. In particular, it is possible to register a three-dimensional anatomical map or electroanatomical map with a three-dimensional ultrasound image with this module. Furthermore, the ultrasound fan image produced by two-dimensional ultrasound imaging shares the coordinate system of the anatomical or electroanatomical map. The system is able to automatically compute the intersection of the fan image and the three-dimensional image, as well as interpolate between adjacent intersections of different fan images.

Operation

Figure 3:
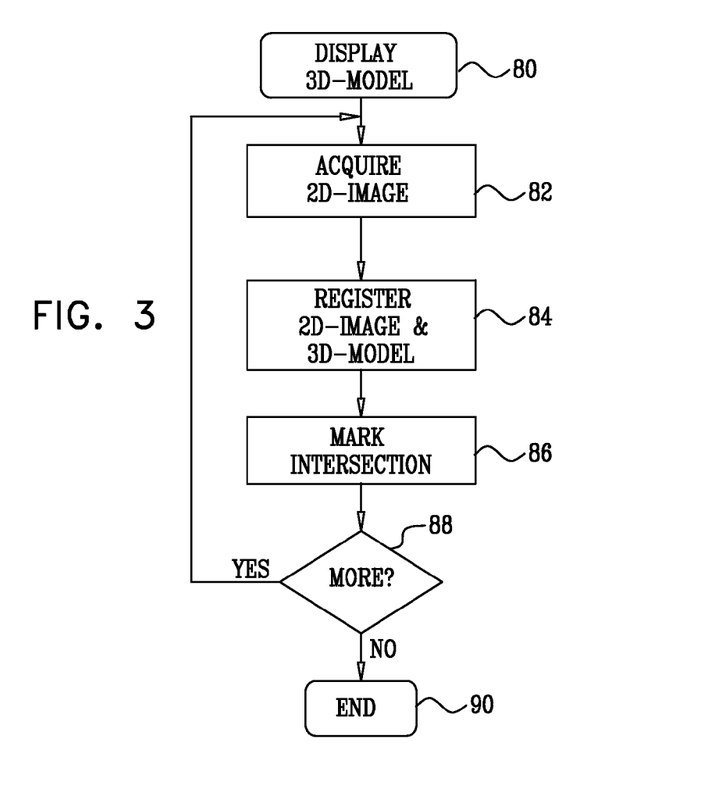
FIG. 3 is a flow chart of a general method of marking a three-dimensional model of an internal structure of the body to indicate progress in acquiring a plurality of two-dimensional images of the structure in accordance with a disclosed embodiment of the invention.

Reference is now made to FIG. 3, which is a flow chart of a general method of marking a three-dimensional model of an internal structure of the body to indicate progress in acquiring a plurality of two-dimensional images of the structure in accordance with a disclosed embodiment of the invention.

At initial step 80, a three-dimensional model of the structure is acquired and displayed. This can be an image of the heart, obtained with a system such as the above-noted CARTO XP EP Navigation and Ablation System. However any three-dimensional model can be used, for example a tomographic image. It is important to display the topography of the heart or other structure, and the functional data, for example electrical potentials that may be shown on the model are incidental.

Next, at step 82 a two-dimensional image of a portion of the structure is acquired. This may be an ultrasound image. Alternatively, the two-dimensional image could be a two-dimensional functional image, obtained by techniques such as magnetic resonance imaging or computed tomographic imaging.

Next, at step 84, the two-dimensional image acquired in step 82 is automatically registered or otherwise coordinated with the three-dimensional model produced in initial step 80. This step allows topographic features of the three-dimensional model to be related to the structures imaged in step 82.

Next, at step 86, the intersection of the plane of the two-dimensional image with the three-dimensional model is marked on the display. This step can be performed by applying a pseudocolor to the display. Alternatively, many other graphical techniques can be used to indicate the intersection, e.g., flashing effects, bolding emphasis. Additionally, as explained below, pseudocolor may be applied in order to display areas on the three-dimensional model located between adjacent intersections of different fan images. Such areas are identified by interpolation. In any case, the operator can identify topographical features of the structure that were obtained on the current two-dimensional image by reference to the display and the markings on the three-dimensional model. Optionally, the operator may annotate the display by textual descriptive information relating to the current two-dimensional image.

Control now proceeds to decision step 88, where it is determined if more images are required to complete the imaging study. If the determination at decision step 88 is affirmative, then control returns to step 82 for another iteration.

If the determination at decision step 88 is negative, then control proceeds to final step 90, and the procedure ends.

Alternate Embodiment 1

Figure 4:
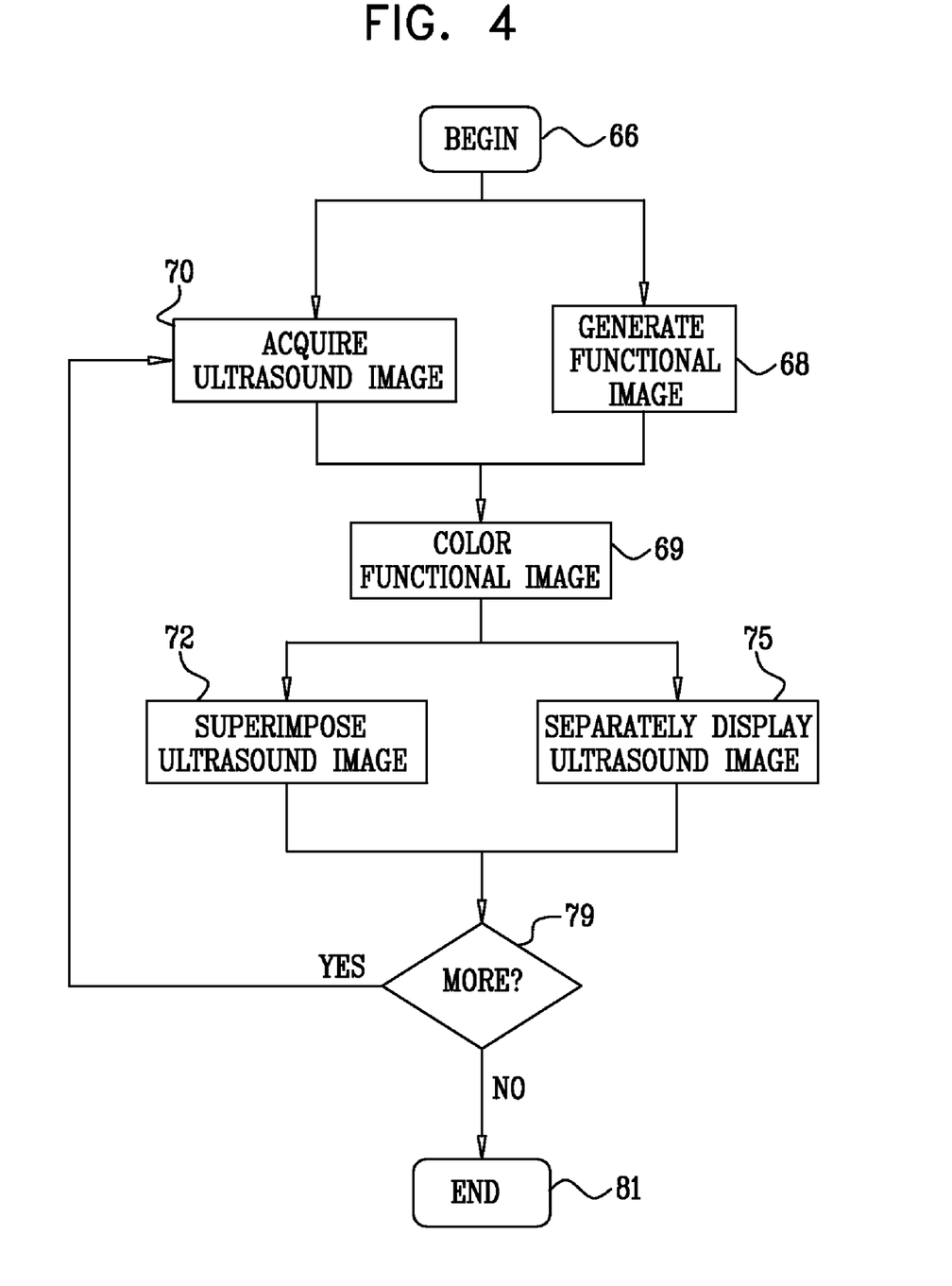
FIG. 4 is a detailed flow chart of a method of coloring a functional map to indicate ultrasound data acquisition in accordance with an alternate embodiment of the invention.

Reference is now made to FIG. 4, which is a detailed flow chart of a method of coloring an electroanatomical map or other functional map to indicate ultrasound data acquisition in accordance with an alternate embodiment of the invention. It will be understood that "coloring", also referred to herein as the application of pseudocolor, denotes a computing task and involves modifications to memory in which image data is stored. The results of the operation may be visualized on a computer monitor as a colored display. The method is discussed with reference to an electroanatomical map by way of example. However, the method is applicable to other functional images of the heart, so long as the topology of the heart is shown and can be related to the location of the ultrasound data. In initial step 66, using instrumentation described above with reference to FIG. 1 and FIG. 2, a mapping catheter is introduced into a subject using well-known techniques. An ultrasound imaging catheter is also introduced into the heart.

Next, at step 68, the mapping catheter is navigated within the heart, and electrical data obtained. A functional image is generated. In one embodiment, an electroanatomical map is generated, for example, using the above-mentioned CARTO XP EP Navigation and Ablation System. The image is generated using the mapping catheter by determining spatial coordinates of different locations in the heart to define a three-dimensional space. Then a functional model is prepared, which is a three-dimensional map of the heart in the three-dimensional space, in which the map displays functional information, i.e., electrical potentials at multiple points of the heart.

Concurrently with step 68, at step 70, at least one two-dimensional ultrasound image is acquired. Generally, this is a gated image. Position information provided by location sensors on the ultrasound imaging catheter are processed by the positioning subsystem to establish coordinates of different points on the ultrasound image. Typically, the electroanatomical map and the two-dimensional ultrasound image are obtained during the same session. However, this is not necessary, and alternatively, the electroanatomical map may be pre-acquired and registered with the two-dimensional ultrasound image.

Next, at step 69, the area of the electroanatomical map or other functional image corresponding to the ultrasound image acquired in the last iteration of step 70 is identified by application of pseudocolor. One pseudocolor may be used, at different intensities as the sufficiency of the image improves. Alternatively, multiple pseudocolors can be used and combined in order to indicate current image quality in many different schemes. Additionally or alternatively, other graphical indications of image quality may be displayed in this step, for example flashing effects. In one embodiment, the relevant portion of the electroanatomical map is determined by computing the plane of intersection of the ultrasound fan image on the electroanatomical map.

Figure 5:
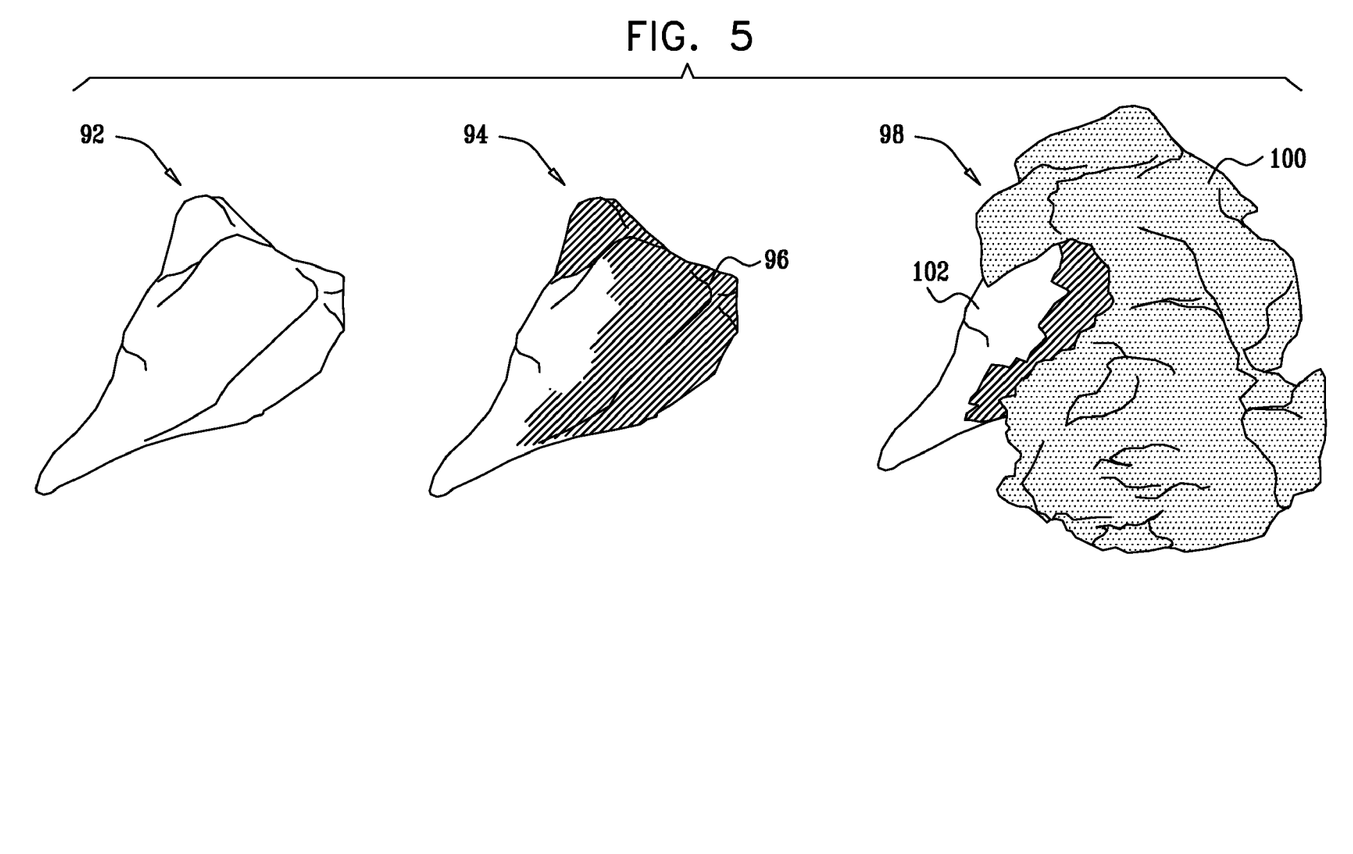
FIG. 5 is a display of multimodal images of the heart in accordance with a disclosed embodiment of the invention.

Reference is now made to FIG. 5, which is a display of multimodal images of the heart in accordance with a disclosed embodiment of the invention. An image 92, at the left side of FIG. 5, is a topological map of a heart chamber generated by the above-noted CARTO XP EP Navigation and Ablation System.

In a central image 94, the map is partly colored to show an area 96 of the chamber wall where ultrasound data have been collected. For example, the plane of intersection of each successive ultrasound two-dimensional fan that is acquired may be marked on the image 94 as a colored region on the map surface. Alternatively, the plane of intersection may be marked as a colored line. Further alternatively, the image 94 may be colored to mark every data voxel where the ultrasound beam plane intersected the electroanatomical map. In any case, the display enables the operator to see where sufficient ultrasound data have been captured and is useful to guide the operator to areas of the heart chamber where additional data collection is still needed.

An image 98 on the right of FIG. 5 shows a reconstruction of a three-dimensional ultrasound image 100 superimposed on the image 98, which is here referenced as an area 102. The image 98 and the area 102 are based on the collected ultrasound data.

In one embodiment, two-dimensional ultrasound images are projected without reconstructing a solid three-dimensional model. This technique is described in the above-noted application Ser. Nos. 11/115,002 and 11/262,217. For example, successive two-dimensional ultrasound images can be acquired in iterations of step 70 (FIG. 4), and contours-of-interest tagged. The images can then be oriented and projected in three-dimensional space.

Figure 6:
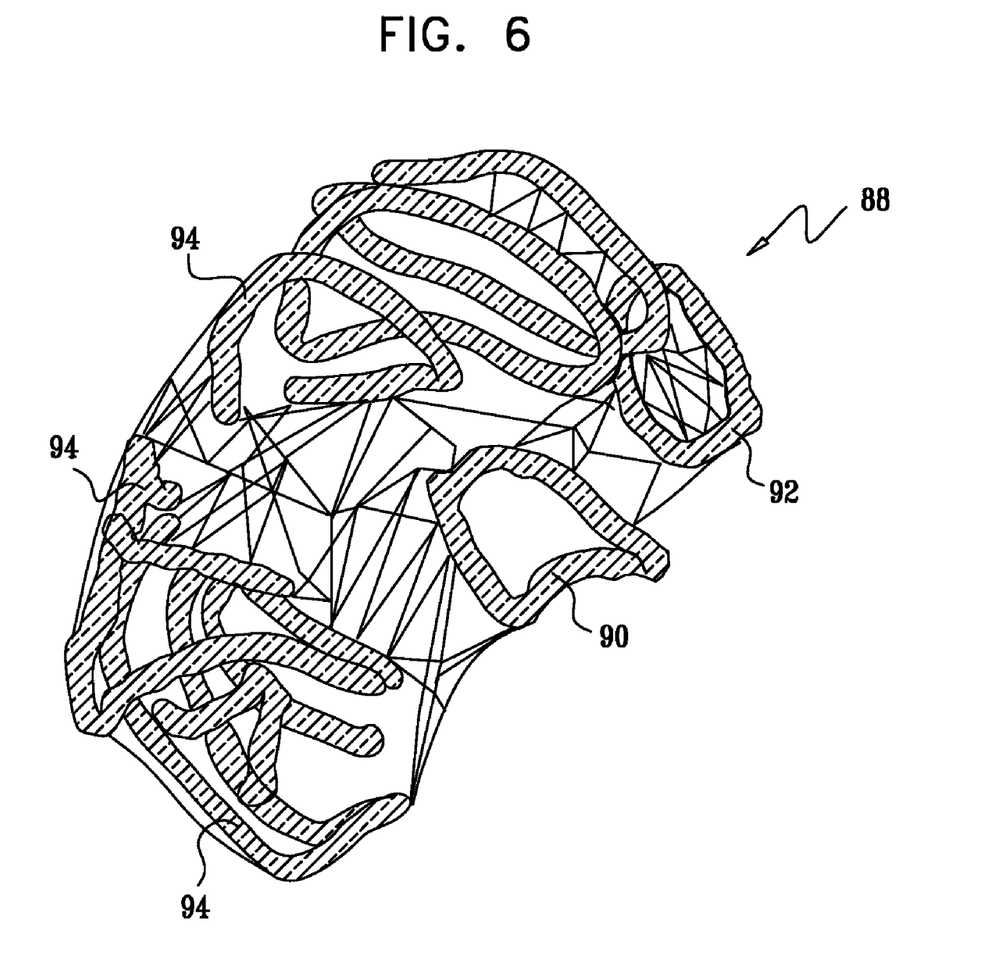
FIG. 6 shows a skeleton model of the right ventricle of a heart, which is prepared in accordance with a disclosed embodiment of the invention.

Reference is now made to FIG. 6, which shows a skeleton model 88 of the right ventricle of a heart, in accordance with a disclosed embodiment of the invention. The system 20 (FIG. 1) can automatically trace and reconstruct contours 90, 92 from untagged ultrasound images and can automatically reconstruct contours 94 from two-dimensional physician-labeled counterparts.

Figure 7:
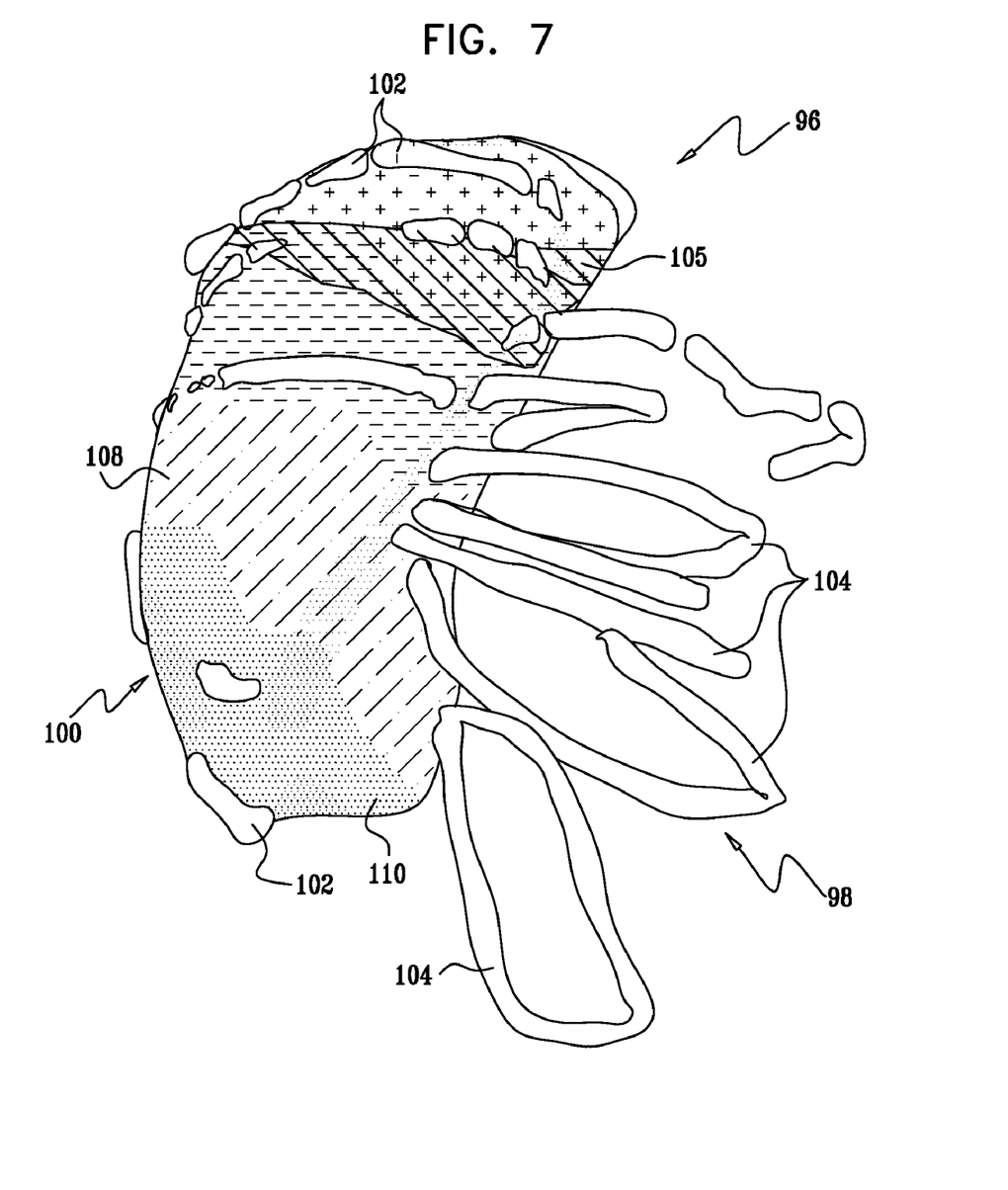
FIG. 7 is a composite image, in which a skeleton model representing of a three-dimensional ultrasound cardiac image of the heart is superimposed on an electro-anatomical map of the right ventricle, in accordance with a disclosed embodiment of the invention.

Reference is now made to FIG. 7, which is an exemplary composite image 96 in which a skeleton model of a three-dimensional ultrasound image 98 of the heart is superimposed on an electro-anatomical map 100 of the right ventricle, in accordance with a disclosed embodiment of the invention. The skeleton model is similar to the skeleton model 88 (FIG. 6), having a plurality of contours 102, 104 outlining the right ventricle and left ventricle, respectively. The contours 102 are overlaid on the electroanatomical map. Different electrical potential values are indicated by different shading patterns. Superimposing the skeletal model on the electroanatomical map in step 72 (FIG. 4) results in less interference on the display than using a fully reproduced three-dimensional model, as can be appreciated by a comparison of FIG. 7 with the image 98 (FIG. 5). As in FIG. 5, portions of the map 100 may be automatically marked using pseudocolor to indicate adequate ultrasound data collection. For example, pseudocolor has been applied to an area 105, represented by a diagonally hatched pattern in FIG. 7.

Referring again to FIG. 4, as the data are acquired in successive iterations of step 70, the electroanatomical map, and optionally vessels, which may be shown diagrammatically on the electroanatomical map as contours or cylindrical structures, are progressively colored to indicate the areas that were imaged, as shown on the image 94 (FIG. 5). For example, the map may start with a gray color, as on the image 92 (FIG. 5), and the color may then change from gray to red at every point on the map that corresponds to points where ultrasound image data were acquired. In this manner, the operator receives a clear indication of the current data coverage.

Next, at step 72, the ultrasound images acquired in iterations of step 70 are superimposed on the electroanatomical map, such that the two are seen in registration on a display. This is carried out automatically, using methods of synchronization, and registration of the reconstructed image with the electroanatomical map, as noted above. Briefly, the ultrasound catheter includes both a location sensor and an ultrasound transducer in one unit. The system, after appropriate calibration, can automatically correlate any point seen on the ultrasound image with its corresponding point in three-dimensional space of the electroanatomic map. The image registration is typically established by correlating the coordinates during the generation of the electroanatomic map with position information and coordinates on the ultrasound image that were obtained in step 70. External anatomic markers may be used to provide a common frame of reference in order to couple the data from the two modalities. In some embodiments, the ultrasound image is a three-dimensional ultrasound image that is reconstructed from multiple two-dimensional ultrasound images. Alternatively, two-dimensional fan images are superimposed as lines on the electroanatomical map.

Optionally, as shown in step 75, the ultrasound images and the electroanatomical map are displayed separately. This option has the advantages that multimodal image registration issues are avoided in the display. Furthermore, one image is not obscured by the other. In a variation of step 75, at least a portion of the three-dimensional image is displayed inside the three-dimensional model, and the three-dimensional image does not extend more than a predefined distance from the surface of the three-dimensional model. The result is that a three-dimensional space is segmented according to the proportion of the three-dimensional image that is displayed. Segmentation techniques suitable for this operation are disclosed in the above-noted application Ser. No. 11/215,435.

In either of steps 72, 75 synchronization between the two modalities required, of course. Referring again to FIG. 7, the ultrasound image 98 and the electroanatomical map 100 can be acquired using different equipment. When one or both of the images are being tracked in near-real time, and particularly when different equipment is used for the two modalities, propagation delays between the source equipment and the processor 36 (FIG. 1) necessitate careful attention to synchronization of the two components of the composite image 96. Indeed, synchronization issues occur generally, in different embodiments of the system 20 (FIG. 1). Solutions for this problem are taught in the above-noted application Ser. No. 11/262,217. Briefly, when near real-time electro-anatomical data are acquired and superimposed upon previously acquired anatomic images or models, a constant pre-defined offset, which can be a temporal offset, is established between the electroanatomical data and the anatomic image gating. This offset compensates for system delays caused by image processing and image transfer from the source of the anatomic images to the image processor, which as noted above, generates an electroanatomical map from the electroanatomical data.

After performing either of steps 72, 75, the operator may identify anatomical features and mark them on the display, using a graphical user interface.

Control next proceeds to decision step 79, where it is determined if more two-dimensional ultrasound images are necessary to complete the examination. This decision is normally made by the operator, but he may be prompted by the system, which can automatically determine if the examination is complete. If the determination at decision step 79 is affirmative, then control returns to step 70. When imaging the heart, the operator may start the imaging procedure with contour mapping of the left and right atria, marking relevant structures, such as the pulmonary veins, aorta and fossa ovalis. The pulmonary veins and aorta can be shown as vessels with adjustable radii defined by the ultrasound contours.

If the determination at decision step 79 is negative, then control proceeds to final step 81. The catheters are withdrawn, and the procedure ends.

Alternate Embodiment 2

This embodiment is similar to alternate embodiment 1, except that an inverse display mode can be used for displaying a three-dimensional image, e.g., the image 100 (FIG. 5) in steps 72, 75 (FIG. 4). The data acquisition for the ultrasound images is essentially the same, but instead of showing high gray scale levels for tissue, the three-dimensional ultrasound image indicates the blood in the chamber or vessel, and is an indicator of the chamber or vessel blood volume.

Alternate Embodiment 3

Other physiological data that may be mapped for co-display in steps 72, 75 (FIG. 4) with ultrasound images and pseudocolor applied colored to indicate sufficiency of ultrasound data collection as described above. Volumetric intraluminal ultrasound imaging as described by the above-noted U.S. Pat. No. 6,066,096 can be used. Other physiological parameters that can be mapped include temperature, blood flow rate, chemical properties and mechanical activity, e.g., regional wall motion. For example, areas of high-speed flow detected by an ultrasound catheters, as disclosed, e.g., in the above-noted U.S. Pat. Nos. 6,716,166 and 6,773,402, may be identified in a Doppler image and registered with stenoses in blood vessels observed in a three-dimensional ultrasound image. As another example, a chemical sensor may be used to identify areas of the heart with low NADPH levels, indicative of ischemia. Such areas may be registered with corresponding areas observed on ultrasound images. The technique described in the article Quantitative Measurements of Cardiac Phosphorus Metabolites in Coronary Artery Disease by 31P Magnetic Resonance Spectroscopy, Takahiro Yabe et al., Circulation. 1995; 92:15-23 is suitable for displaying such areas.

Alternate Embodiment 4

In this embodiment, step 70 (FIG. 4) is performed using a modality other than two-dimensional ultrasound imaging to acquire realtime data as a series of image "slices" through the target structure. Step 70 can be performed using a realtime three-dimensional ultrasound imaging probe, realtime computed tomographic imaging, realtime magnetic resonance imaging or other realtime imaging modality from which three-dimensional images can be generated and co-displayed with a functional image to which pseudocolor is applied to indicate sufficiency of data imaging in particular areas.

Alternate Embodiment 5

This variation can be employed additionally to any of the preceding embodiments. In steps 72, 75 (FIG. 4), additional indications are shown on the map display to guide the operator during data acquisition. For example, the fill ratio, the ratio of colored area to total target area on the electroanatomical map or other functional map, can be displayed to quantitatively indicate the extent of completion of the session.

In additional application of pseudocolor itself can be modified according to the gray scale level of each voxel using a corresponding lookup table. This enables the user to see if the acquired data corresponds to a wall tissue or to a vessel or valve opening in the chamber.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A computer-assisted method for producing images of a living subject, comprising the steps of:
   displaying a three-dimensional model of a surface of a structure in a body of said subject;
   acquiring a sequence of two-dimensional images of at least a portion of said structure, said two-dimensional images having respective image planes;
   while acquiring said sequence, marking said three-dimensional model to show respective intersections of said image planes with said surface;
   wherein said two-dimensional images are acquired as realtime images by acquiring a plurality of two-dimensional ultrasound slices, computed tomographic slices, or realtime magnetic resonance slices, further comprising the steps of constructing three-dimensional images from said realtime images for use in said step of displaying.

2. The method according to claim 1, wherein said two-dimensional images are selected from the group consisting of two-dimensional ultrasound images, computed tomographic images and magnetic resonance images.

3. The method according to claim 1, further comprising the step of displaying said three-dimensional model and said respective intersections of said image planes with said surface on said three-dimensional model.

4. The method according to claim 3, wherein displaying said three-dimensional model comprises applying a pseudocolor to said respective intersections of said image planes with said surface.

5. The method according to claim 3, wherein marking said three-dimensional model comprises the steps of:
   interpolating areas of said three-dimensional model between said respective intersections;
   marking said interpolated areas, and
   said step of displaying said three-dimensional model comprises displaying said interpolated areas.

6. The method according to claim 1, further comprising the steps of:
   reconstructing a three-dimensional anatomic image of said structure from said two-dimensional images; and
   displaying at least a portion of said three-dimensional anatomic image with said three-dimensional model.

7. The method according to claim 6, wherein said portion of said three-dimensional anatomic image does not extend beyond a predefined distance from a surface of said three-dimensional model.

8. The method according to claim 1, wherein said structure is a heart and said three-dimensional model is an anatomical map.

9. An apparatus for producing images of a living subject comprising:
   a display; a memory for storing a three-dimensional model of a surface of a structure in a body of said subject;
   a two-dimensional imaging module operative for acquiring a sequence of two-dimensional anatomic images of at least a portion of said structure, said two-dimensional anatomic images having respective image planes;
   a processor linked to said memory and to said two-dimensional imaging module, said processor operative for marking said three-dimensional model on said display to show respective intersections of said image planes with said surface; and
   wherein said two-dimensional images are acquired as real-time images by acquiring a plurality of two-dimensional ultrasound slices, computed tomographic slices, or real-time magnetic resonance slices, and wherein said three-dimensional images are constructed from said realtime images for use on the display.

10. The apparatus according to claim 9, wherein said processor is operative for automatically registering said image planes with said three-dimensional model.

11. The apparatus according to claim 9, wherein said processor is operative for:
   reconstructing a three-dimensional anatomic image of said structure from said two-dimensional anatomic images; and
   displaying said three-dimensional anatomic image with said three-dimensional model.

12. The apparatus according to claim 9, wherein said two-dimensional imaging module generates ultrasound images, said structure is a heart and said three-dimensional model is an electroanatomical map.

13. A computer-assisted method for producing images of a living subject, comprising the steps of:
   introducing a probe into a heart of said subject, said probe having a location sensor;
   with said probe determining respective spatial coordinates of different locations in said heart to define a three-dimensional space;
   generating a functional model comprising a three-dimensional map of said heart comprising functional information relating to said heart measured at multiple points of said heart;
   acquiring an ultrasound image of a portion of said heart;
   registering said ultrasound image with said three-dimensional space;
   automatically marking a region on said map that corresponds to said portion of said heart; and
   displaying said ultrasound image and said map, wherein said region is shown in a pseudocolor.

14. The method according to claim 13, wherein said functional model is selected from the group consisting of an anatomical map, a volumetric intraluminal ultrasound image, a Doppler image, and a regional wall motion image.

15. The method according to claim 13, wherein said ultrasound image is a two-dimensional ultrasound image, and said step of automatically marking a region comprises determining an intersection of a plane of said two-dimensional ultrasound image with said map.

16. The method according to claim 15, wherein said step of acquiring an ultrasound image comprises acquiring a plurality of two-dimensional ultrasound images of respective portions of said heart, the method further comprising the steps of:
   reconstructing a three-dimensional anatomic image of said heart from said two-dimensional ultrasound images;
   iterating said step of automatically marking a region using respective ones of said two-dimensional ultrasound images to define a composite marked region; and
   said step of displaying comprises displaying said three-dimensional anatomic image with said map, wherein said composite marked region is shown in said pseudocolor.

17. The method according to claim 13, said step of displaying comprises displaying said ultrasound image superimposed on said map.

18. An apparatus for imaging a heart in a body of a subject, comprising:
   an imaging device for capturing an anatomic image of a portion of said heart;
   a processor linked to said imaging device, said processor being linked to a probe adapted for insertion into said heart and having a position sensor for determining position and orientation information of said probe, said processor being operative for generating a functional map of said heart comprising functional information relating to said heart measured at multiple points on said heart, said processor being operative for automatically marking a region of said map that corresponds to of said portion of said heart; and
   a display device linked to said processor for displaying said map and said anatomic image, wherein said region is displayed in a pseudocolor.

19. The apparatus according to claim 18, wherein said functional map is an electroanatomical map.

20. The apparatus according to claim 18, wherein said imaging device is operative for acquiring a plurality of two-dimensional anatomic images of respective portions of said heart.

21. The apparatus according to claim 20, wherein said processor is operative for:
   reconstructing a three-dimensional anatomic image of said heart from said two-dimensional anatomic images;

iteratively automatically marking a region using respective ones of said two-dimensional anatomic images to define a composite marked region; and said display device is operative for displaying said three-dimensional anatomic image with said map, wherein said composite marked region is shown in said pseudo-color.

22. A computer-assisted method for producing images of a living subject, comprising the steps of:

displaying a three-dimensional model of a surface of a structure in a body of said subject;

acquiring a sequence of three-dimensional anatomic images of respective portions of said structure, said three-dimensional anatomic images having respective image planes;

while acquiring said sequence, automatically registering said image planes with said three-dimensional model;

marking said three-dimensional model to show respective intersections of said three-dimensional anatomic images with said surface; and wherein said three-dimensional anatomic images are acquired as realtime images by acquiring a plurality of two-dimensional ultrasound slices, computed tomographic slices, or realtime magnetic resonance slices, further comprising the steps of constructing said three-dimensional anatomic images from said realtime images for use in said step of displaying.

23. The method according to claim 22, wherein said sequence is acquired using an ultrasound probe.

* * * * *